United States Patent
Rister, Jr. et al.

(10) Patent No.: US 10,766,994 B2
(45) Date of Patent: Sep. 8, 2020

(54) REDUCTION OF ALDEHYDES IN AMINE CATALYSTS

(71) Applicant: HUNTSMAN PETROCHEMICAL LLC, The Woodlands, TX (US)

(72) Inventors: Ernest L. Rister, Jr., Round Rock, TX (US); Haibo Zhao, The Woodlands, TX (US); Robert A. Grigsby, Jr., Spring, TX (US); Robert B. Moore, Liberty Hill, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 222 days.

(21) Appl. No.: 15/534,814

(22) PCT Filed: Jan. 13, 2015

(86) PCT No.: PCT/US2015/011163
§ 371 (c)(1),
(2) Date: Jun. 9, 2017

(87) PCT Pub. No.: WO2016/108941
PCT Pub. Date: Jul. 7, 2016

(65) Prior Publication Data
US 2018/0355093 A1    Dec. 13, 2018

Related U.S. Application Data

(60) Provisional application No. 62/098,380, filed on Dec. 31, 2014.

(51) Int. Cl.
| | | |
|---|---|---|
| C07C 209/80 | (2006.01) | |
| C08G 18/18 | (2006.01) | |
| C08G 18/48 | (2006.01) | |
| C08G 18/76 | (2006.01) | |
| C08G 18/50 | (2006.01) | |
| C08G 18/32 | (2006.01) | |
| C07C 209/84 | (2006.01) | |
| C08G 101/00 | (2006.01) | |

(52) U.S. Cl.
CPC ........ C08G 18/1833 (2013.01); C07C 209/84 (2013.01); C08G 18/18 (2013.01); C08G 18/1825 (2013.01); C08G 18/3218 (2013.01); C08G 18/3228 (2013.01); C08G 18/4816 (2013.01); C08G 18/4841 (2013.01); C08G 18/5024 (2013.01); C08G 18/7664 (2013.01); C08G 2101/005 (2013.01)

(58) Field of Classification Search
CPC .... C07C 209/84; C08G 18/10; C08G 18/384; C08G 18/721; C08G 18/2875; C08G 18/3293; C08G 18/1833; C08G 18/4841; C08G 18/3218
See application file for complete search history.

(56) References Cited

U.S. PATENT DOCUMENTS

| | | | |
|---|---|---|---|
| 4,154,724 A * | 5/1979 | Schulze | C07C 275/04 528/68 |
| 4,705,814 A | 11/1987 | Grigsby, Jr. et al. | |
| 5,506,329 A | 4/1996 | Chou et al. | |
| 7,879,928 B2 | 2/2011 | Goh et al. | |
| 2006/0141236 A1 | 6/2006 | Nakamura et al. | |
| 2008/0281013 A1 | 11/2008 | Nakamura et al. | |
| 2009/0227758 A1 | 9/2009 | Miyazaki | |
| 2009/0312450 A1 | 12/2009 | Martin et al. | |
| 2009/0326089 A1 | 12/2009 | Haas et al. | |
| 2011/0009512 A1 * | 1/2011 | Grigsby, Jr. | C08G 18/1808 521/94 |
| 2011/0009513 A1 | 1/2011 | Chaudhary et al. | |
| 2011/0040043 A1 | 2/2011 | Ito et al. | |
| 2012/0271026 A1 * | 10/2012 | Barman | C08G 18/1825 528/49 |
| 2013/0085193 A1 | 5/2013 | Burdeniuc et al. | |
| 2013/0137787 A1 | 5/2013 | Burdeniuc et al. | |
| 2013/0203880 A1 | 8/2013 | George et al. | |

FOREIGN PATENT DOCUMENTS

| | | |
|---|---|---|
| CN | 102741310 | 10/2012 |
| DE | 102008025005 A1 | 11/2009 |
| WO | 2009114329 A2 | 9/2009 |

* cited by examiner

*Primary Examiner* — Michael L Leonard
(74) *Attorney, Agent, or Firm* — Huntsman Petrochemical LLC; Lewis Craft

(57) ABSTRACT

The present disclosure provides a method for reducing the aldehyde content in an amine catalyst by treating the amine catalyst with a treating agent selected from a non-cyclic amide substituted with an isocyanate reactive group, a guanidine substituted with an isocyanate reactive group, a polyether amine adducted with a urea compound or a guanidine compound, a free radical scavenger and a mixture thereof. The treated amine catalyst may then be used in the production of polyurethane materials which exhibit reduced aldehyde emissions.

7 Claims, No Drawings

REDUCTION OF ALDEHYDES IN AMINE CATALYSTS

CROSS-REFERENCE TO RELATED APPLICATIONS

This application is the National Phase of International Application PCT/US2015/011163 filed Jan. 13, 2015 which designated the U.S. and which claims priority to U.S. App. Ser. No. 62/098,380 filed Dec. 31, 2014. The noted applications are incorporated herein by reference.

FIELD OF THE INVENTION

The present disclosure is directed to amine catalysts exhibiting low levels of aldehydes and to polyurethane materials produced using such amine catalysts.

BACKGROUND INFORMATION

Emissions from polyurethane foam are a concern in many applications, especially when workers or end users are exposed to the foam within an enclosed space. Aldehyde emissions, such as formaldehyde, are a particular cause of concern. To reduce such aldehyde emissions, several methods have been developed to reduce the aldehyde content of the raw materials used in producing polyurethane foam. For example: U.S. Pat. No. 7,879,928 discloses a method for preventing the formation of aldehyde compounds in polyether or polyester polyols by incorporating a phenolic antioxidant and an aminic antioxidant into the polyol; U.S. Pat. Publ. No. 2009/0227758 discloses a method of reducing aldehydes in polyols and polyisocyanates by reacting the polyol with an oxazolidine-forming amino alcohol and the polyisocyanate with a nitroalkane; U.S. Pat. App. No. 2006/0141236 discloses the addition of a hydrazine to a polyol to act as an aldehyde-scavenger; U.S. Pat. App. No. 2008/0281013 discloses a method for reducing aldehyde emissions from a polyurethane foam by the addition of hydrogen sulfites and disulfites to the polyol component; U.S. Pat. App. No. 2009/0326089 discloses the use of a compound having a carbon amide group and a nitrile group to produce foams having a lowered emission of formaldehyde; WO2009/114329 teaches the addition of an oxazolidine-forming amino alcohol to a polyol and a nitroalkane to a polyisocyanate to reduce aldehyde emissions prior to their reaction in the production of a polyurethane; U.S. Pat. App. No. 2013/0203880 which teaches the addition of a polyhydrazodi-carbonamide polyol to the polyol component or a trimerized hexamethylene diisocyanate to the polyisocyanate component results in foams exhibiting decreased aldehyde emissions; and U.S. Pat. No. 5,506,329 discloses the use of certain aldimine oxazolidine compounds for scavenging formaldehyde from polyisocyanate-containing preparations.

In addition to polyols and polyisocyanates, amine catalysts are often utilized as a raw material in the production of polyurethane foam. The aldehydes found in amine catalysts may be derived from a variety of sources, for example, they may be present as a contaminant from the manufacture of the amine, or they may result from the oxidation or free radical attack of various carbon segments of the amine during storage. Methods to reduce the aldehyde content in amine catalysts include the use of inert gas (see U.S. Pat. Publ. No. 2013/0085193), primary amines (see U.S. Pat. Publ. No. 2011/0009513) free radical scavengers (see U.S. Pat. Publ. No. 2012/0271026) and combining an amine which has urea, amide, secondary-amine, primary amine or secondary-hydroxyl functionality with a carboxylic diacid or triacid (see U.S. Pat. Publ. No. 2013/0137787). Additionally, DE102008025005 teaches the use of urea nanoparticles in the treatment of amine catalysts to remove formaldehyde; however, when the amine catalyst is subsequently used in the production of foam, the urea is found as an emission in the foam and therefore the foam will generally fail environmental specifications for total emissions.

Despite the state of the art, there is a continuing need for developing other inexpensive and effective methods to reduce the aldehyde content in amine catalysts. Preferably, such methods do not result in significant changes to the properties or performance of the amine catalyst or the resulting polyurethane foam. Moreover, preferably such methods do not produce other fugitive species which may provide additional environmental, health and safety issues to the amine catalyst and resulting polyurethane foam.

SUMMARY OF THE INVENTION

The present disclosure relates to a method for reducing the aldehyde impurities from an amine catalyst by treating the amine catalyst with a treating agent selected from a non-cyclic amide substituted with an isocyanate reactive group, a guanidine substituted with an isocyanate reactive group, a polyether amine adducted with a urea compound or a guanidine compound, a free radical scavenger and a mixture thereof and subjecting the resulting mixture to conditions such that the level of aldehyde impurities in the amine catalyst is reduced.

In a further embodiment, the present disclosure provides a method for reducing the aldehyde emissions from a polyurethane material by reacting a polyisocyanate and polyol in the presence of the treated amine catalyst above.

In a still further embodiment, the present disclosure provides a packaged product comprising a container and a catalyst mixture within the container, the catalyst mixture comprising an amine catalyst and a treating agent selected from a non-cyclic amide substituted with an isocyanate reactive group, a guanidine substituted with an isocyanate reactive group, a polyether amine adducted with a urea compound or a guanidine compound, a free radical scavenger and a mixture thereof and wherein the amine catalyst and treating agent have been subjected to conditions such that the level of aldehyde impurities in the amine catalyst has been reduced.

DETAILED DESCRIPTION

If appearing herein, the term "comprising" and derivatives thereof are not intended to exclude the presence of any additional component, step or procedure, whether or not the same is disclosed herein. In order to avoid any doubt, all formulations claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or to more than one (i.e. to at least one) of the grammatical object of the article. By way of example, "a free radical scavenger" means one free radical scavenger or more than one free radical scavenger.

The phrases "in one embodiment," "according to one embodiment," and the like generally mean the particular feature, structure, or characteristic following the phrase is included in at least one embodiment of the present invention, and may be included in more than one embodiment of the present invention. Importantly, such phrases do not necessarily refer to the same embodiment.

If the specification states a component or feature "may", "can", "could", or "might" be included or have a characteristic, that particular component or feature is not required to be included or have the characteristic.

For methods of treating an amine catalyst, the term "treating" includes placing a component onto the amine catalyst using any suitable manner known in the art, including, but not limited to, pumping, injecting, pouring, releasing, displacing, squeezing, spotting, or circulating the component onto the amine catalyst.

The term "isocyanate reactive group" as used herein includes any group or moiety containing an active hydrogen group or moiety. For the purposes of this disclosure, an active hydrogen containing group refers to a group containing a hydrogen atom which, because of its position in the molecule, displays significant activity according to the Zerewitnoff test described by Wohler in the Journal of the American Chemical Society, Vol. 49, page 3181 (1927). Illustrative of such active hydrogen groups are —COOH, —OH, —NH$_2$, and —NH.

The term "non-cyclic amide" means an amide compound that does not comprise a closed ring structure.

The term "polyamine" means a compound comprising two or more primary or secondary amine groups per molecule.

The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" means a mono-, di-, or polynuclear aromatic hydrocarbon group. The term "heterocyclic group" means a closed ring hydrocarbon in which one or more of the atoms in the ring is an element other than carbon (for e.g., nitrogen, oxygen, sulfur, etc.).

In one aspect, the present disclosure provides a method for reducing the aldehyde content in an amine catalyst by treating an amine catalyst containing one or more aldehyde impurities with a treating agent selected from a non-cyclic amide substituted with an isocyanate reactive group, a guanidine substituted with an isocyanate reactive group, a polyether amine adducted with a urea compound or a guanidine compound, a free radical scavenger and a mixture thereof to form a catalyst mixture and subjecting the catalyst mixture to conditions such that the level of aldehyde impurities in the amine catalyst is reduced.

In another aspect, the present disclosure provides a method for reducing aldehyde emissions from a polyurethane material comprising (i) treating an amine catalyst containing one or more aldehyde impurities with a treating agent selected from a non-cyclic amide substituted with an isocyanate reactive group, a guanidine substituted with an isocyanate reactive group, a polyether amine adducted with a urea compound or a guanidine compound, a free radical scavenger and a mixture thereof to form a catalyst mixture and subjecting the catalyst mixture to conditions such that the level of aldehyde impurities in the amine catalyst are reduced and (ii) reacting a polyol with a polyisocyanate in the presence of the catalyst mixture from step (i) to form a polyurethane material.

In still another aspect, there is provided a packaged product comprising (i) a container having an outlet and (ii) a catalyst mixture within the container comprising a treating agent selected from a non-cyclic amide substituted with an isocyanate reactive group, a guanidine substituted with an isocyanate reactive group, a polyether amine adducted with a urea compound or a guanidine compound, a free radical scavenger and a mixture thereof and an amine catalyst containing one or more aldehyde impurities wherein the catalyst mixture has been subjected to conditions such that the level of aldehyde impurities in the amine catalyst has been reduced. The packaged product may be stored for a long period of time (for e.g. at least about 1 month) and can be used in the manufacture of a polyurethane material.

The present disclosure therefore provides an inexpensive and effective way to reduce the level of aldehyde impurities, such as formaldehyde, in an amine catalyst through treatment with a non-cyclic amide substituted with an isocyanate reactive group, a guanidine substituted with an isocyanate reactive group, a polyether amine adducted with a urea compound or a guanidine compound, a free radical scavenger or a combination thereof. Moreover, the treated amine catalyst exhibits stable color over time as compared to color increase exhibited by untreated amine catalysts. After treatment, the catalyst mixture comprising the amine catalyst and treating agent can be used to catalyze the reaction between a polyol and polyisocyanate to produce a polyurethane material that exhibits reduced aldehyde emissions. It has been surprisingly found that by incorporating an isocyanate reactive group having an active hydrogen compound that is more reactive than the hydrogen compound of a urea group onto the treating agent allows the treating agent to remain bound in the polyurethane material thus preventing it from becoming a volatile organic contaminant, yet allowing it to still remain active as a scavenger for aldehydes.

The amine catalyst of the present disclosure may be any amine useful as a catalyst in a polyurethane material formation reaction. According to one embodiment, the amine catalyst is an amine containing one or more tertiary amino groups. Examples include, but are not limited to, bis-(2-dimethylaminoethyl)ether (JEFFCAT® ZF-20 catalyst), N,N,N'-trimethyl-N'-hydroxyethylbisaminoethylether (JEFFCAT® ZF-10 catalyst), N-(3-dimethylaminopropyl)-N, N-diisopropanolamine (JEFFCAT® DPA catalyst), N, N-dimethylethanolamine (JEFFCAT® DMEA catalyst), triethylene diamine (JEFFCAT® TEDA catalyst), blends of N,N-dimethylethanolamine and triethylene diamine (such as JEFFCAT® TD-20 catalyst), N,N-dimethylcyclohexylamine (JEFFCAT® DMCHA catalyst), benzyldimethylamine (JEFFCAT® BDMA catalyst), pentamethyldiethylenetriamine (JEFFCAT® PMDETA catalyst), N,N,N',N",N"'-pentamethyldipropylenetriamine (JEFFCAT® ZR-40 catalyst), N,N-bis(3-dimethylaminopropyl)-N-isopropanolamine (JEFFCAT® ZR-50 catalyst), N'-(3-(dimethylamino)propyl-N,N-dimethyl-1,3-propanediamine (JEFFCAT® Z-130 catalyst), 2-(2-dimethylaminoethoxy)ethanol (JEFFCAT® ZR-70 catalyst), N,N,N'-trimethylaminoethyl-ethanolamine (JEFFCAT® Z-110 catalyst), N-ethylmorpholine (JEFFCAT® NEM catalyst), N-methylmorpholine (JEFFCAT® NMM catalyst), 4-methoxyethylmorpholine, N, N'dimethylpiperzine (JEFFCAT® DMP catalyst), 2,2'dimorpholinodiethylether (JEFFCAT® DMDEE catalyst), 1,3,5-tris(3-(dimethylamino)propyl)-hexahydro-s-triazine (JEFFCAT® TR-90 catalyst), 1-Propanamine, 3-(2-(dimethylamino)

ethoxy), substituted imidazoles such as 1,2-dimethlyimidazol and 1-methyl-2-hydroxyethylimidazole, N,N'-dimethylpiperazines or bis-substituted piperazines such aminoethylpiperazine, N,N',N'-trimethyl aminoethylpiperazine or bis-(N-methyl piperazine)urea, N-methylpyrrolidines and substituted methylpyrrolidines such as 2-aminoethyl-N-methylpyrrolidine or bis-(N-methylpyrrolidine) ethyl urea, 3-dimethylaminopropylamine, N,N,N",N"-tetramethyldipropylenetriamine, tetramethylguanidine, 1,2 bis-diisopropanol. Other examples of amine catalysts include N-alkylmorpholines such as N-methylmorpholine, N-ethylmorpholine, N-butylmorpholine and dimorpholinodiethylether, N,N'-dimethylaminoethanol, N, N-dimethylamino ethoxyethanol, bis-(dimethylaminopropyl)-amino-2-propanol, bis-(dimethylamino)-2-propanol, bis-(N,N-dimethylamino)ethylether; N,N,N'-trimethyl-N'hydroxyethyl-bis-(aminoethyl)ether, N,N-dimethylaminoethyl-N'-methyl amino ethanol, tetramethyliminobispropylamine and combinations thereof. The aforementioned JEFFCAT® catalysts are available from Huntsman Petrochemical LLC, The Woodlands, and Texas.

The treating agent used in treating the amine catalyst is selected from a non-cyclic amide substituted with an isocyanate reactive group, a guanidine substituted with an isocyanate reactive group, a polyether amine adducted with a urea compound or a guanidine compound, a free radical scavenger and a mixture thereof.

According to one embodiment, the treating agent is a non-cyclic amide substituted with an isocyanate reactive group represented by the general formula (I):

R—(NH)$_n$-A-X    (I)

where X is NHR$^0$,
R and R$^0$ are each independently hydrogen or a linear or branched C$_1$-C$_{30}$ alkyl group having a hydrogen or methylene group substituted with an isocyanate reactive group selected from —OH, —NH, —NH$_2$ and —COOH,
n is 0, 1, or greater than 1 and
A is C═O with the proviso that at least one of R or R$^0$ is other than hydrogen. In one preferred embodiment, R or R$^0$ is a linear or branched C$_1$-C$_{10}$ alkyl group having a terminal hydrogen or a terminal methylene group substituted with an isocyanate reactive group selected from —OH, —NH$_2$ or —COOH.

According to one particular embodiment, the non-cyclic amide substituted with an isocyanate reactive group of the formula (I) is a compound where R is a C$_1$-C$_{30}$ linear or branched alkyl group having a hydrogen or methylene group substituted with —OH, R$^0$ is hydrogen and n=1. In a further embodiment, the non-cyclic amide substituted with an isocyanate reactive group of the formula (I) is a compound where R is a linear or branched C$_1$-C$_{10}$ alkyl group having a terminal hydrogen or terminal methylene group substituted with —OH, R$^0$ is hydrogen and n=1.

In still another embodiment, the non-cyclic amide substituted with an isocyanate reactive group of the formula (I) is a compound where R is a C$_1$-C$_{30}$ linear or branched alkyl group having a hydrogen or methylene group substituted with —NH, R$^0$ is hydrogen and n=1. In a further embodiment, the non-cyclic amide with an isocyanate reactive group of the formula (I) is a compound where R is a linear or branched C$_1$-C$_{10}$ alkyl group having a hydrogen or methylene group substituted with —NH, R$^0$ is hydrogen and n=1.

In yet another embodiment, the non-cyclic amide substituted with an isocyanate reactive group of the formula (I) is a compound where R is a C$_1$-C$_{30}$ linear or branched alkyl group having a hydrogen or methylene group with —NH$_2$, R$^0$ is hydrogen and n=1. In a further embodiment, the non-cyclic amide with an isocyanate reactive group of the formula (I) is a compound where R is a linear or branched C$_1$-C$_{10}$ alkyl group having a terminal hydrogen or terminal methylene group substituted with —NH$_2$, R$^0$ is hydrogen and n=1.

According to another embodiment, the non-cyclic amide substituted with an isocyanate reactive group of the formula (I) is a compound where R is a C$_1$-C$_{30}$ linear or branched alkyl group having a hydrogen or methylene group substituted with —COOH, R$^0$ is hydrogen and n=1. In a further embodiment, the non-cyclic amide with an isocyanate reactive group of the formula (I) is a compound where R is a linear or branched C$_2$-C$_{10}$ alkyl group having a terminal hydrogen or terminal methylene group substituted with —COOH, R$^0$ is hydrogen and n=1.

In still another embodiment, the treating agent is a guanidine substituted with an isocyanate reactive group represented by the general formula (II):

R$^1$R$^2$N-A-X    (II)

where X═NHR$^3$,
R$^1$, R$^2$, and R$^3$ are each independently hydrogen, a linear or branched C$_1$-C$_{30}$ alkyl group of which a hydrogen atom may be further replaced with a substituent group, a C$_5$-C$_{15}$ cyclic group of which a hydrogen atom may be further replaced with a substituent group, and
A is C═NH with the proviso that at least one of R$^1$, R$^2$ or R$^3$ is a linear or branched C$_1$-C$_{30}$ alkyl group or a C$_5$-C$_{15}$ cyclic group each of which having a hydrogen or methylene group substituted with an isocyanate reactive group selected from —OH, —NH, —NH$_2$ and —COOH.

Examples of substituent groups include a C$_1$-C$_{10}$ alkyl group, a C$_3$-C$_8$ carbocyclic group, a C$_1$-C$_{10}$ alkoxy group, an aromatic hydrocarbon group having six to ten carbon atoms, halogen or a nitro.

In another embodiment, the treating agent is a polyether amine adducted with a urea compound or a guanidine compound. In one particular embodiment, the polyether amine adducted with a urea compound or a guanidine compound may be represented by the general formula (III):

R$^4$—NH-A-NH$_2$    (III)

where R$^4$ is a linear or branched alkoxylated polyether polyamine, and
A is C═O or C═NH.

The linear or branched alkoxylated polyether polyamine may be prepared by means well known in the art. For example, the alkoxylated polyether polyamine may be prepared by reacting a polyether polyamine with one or more low molecular weight alkylene oxides, such as ethylene oxide, propylene oxide, butylene oxide, or mixtures thereof, at a temperature from about 100°-110° C. and at a pressure of about 60 psig in the presence of an alkaline catalyst. The polyether polyamine may be alkoxylated to varying degrees. In one embodiment, the resulting alkoxylated polyether polyamine has an alkylene oxide content less than about 90 percent. The alkoxylated polyether polyamine may then be reacted with a urea compound or guanidine compound with heat over a period of time to form the respective adduct.

In one particular embodiment, R$^4$ is an alkoxylated polyether polyamine represented by the general formula (IV):

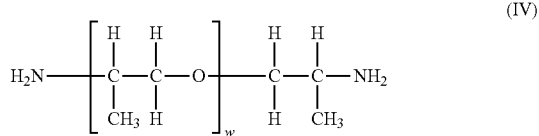

(IV)

where w is an integer ranging from about 1.5 to about 150. In another embodiment, w is an integer ranging from about 2 to about 75. In still another embodiment, w is an integer ranging from about 2.5 to about 70.

In another embodiment, $R^4$ is an alkoxylated polyether polyamine represented by the general formula (V)

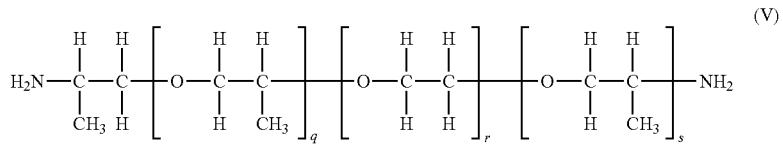

(V)

where r is an integer ranging from about 1.5 to about 50 and the sum of q+s ranges from about 0.5 to about 8. In another embodiment, r is an integer ranging from about 2 to about 40 and the sum of q+s ranges from about 1 to about 6.

In still another embodiment, $R^4$ is an alkoxylated polyether polyamine represented by the general formula (VI):

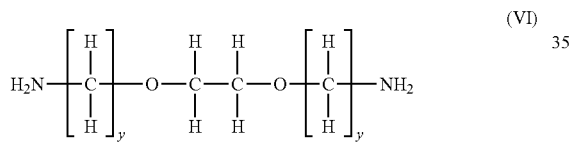

(VI)

where y is an integer ranging from about 1.5 to 4. In another embodiment, y is an integer ranging from about 2 to about 3.

In a further embodiment, $R^4$ is an alkoxylated polyether polyamine represented by the general formula (VII):

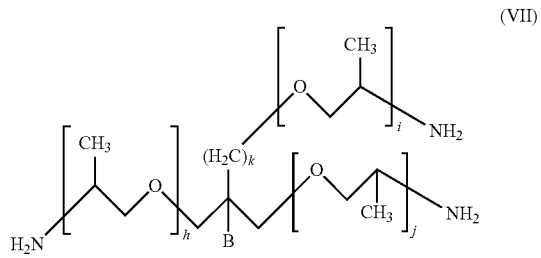

(VII)

where k is 0 or 1,
B is hydrogen or an ethyl group, and
(h+i+j) is an integer from about 4 to 100.

Examples of commercially available alkoxylated polyether polyamines are the JEFFAMINE® D Series, ED Series, T Series and EDR Series amines (Huntsman Petrochemical LLC).

According to another embodiment, the treating agent is a free radical scavenger. The free radical scavenger include compounds such as, but not limited to, methimazole, phenyl methimazole, and derivatives thereof; allupurinol, propyl thiouracil, glutamine, diaminobenzylamine; nicotinamide; hindered phenols or hindered aliphatic or aromatic amines; and natural antioxidants such as Vitamin C, Vitamin E and/or glutathione. According to one embodiment, the free radical scavenger is a sterically hindered phenol. The term "sterically hindered phenol" as used herein means that the phenol in positions 2 and 6 of the aromatic ring has substituents which, on the basis of their three-dimensional size, shield the OH group of the phenolic ring and result in an attenuated reactivity. In one particular embodiment, the sterically hindered phenol is a compound having the formula (VIII):

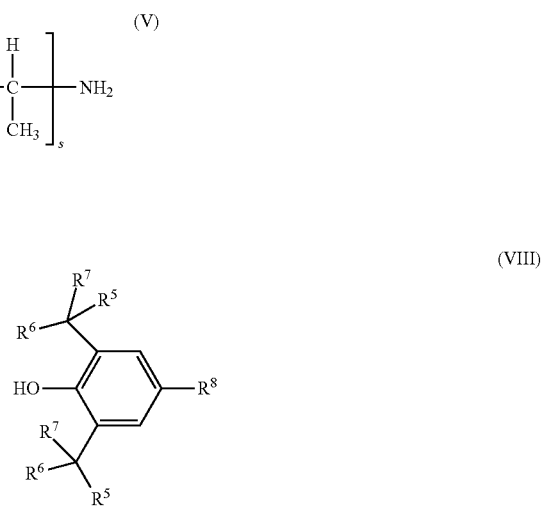

(VIII)

where $R^5$, $R^6$ and $R^7$ are independently selected from H or a $C_1$-$C_{10}$ alkyl group and $R^8$ is H or a $C_1$-$C_{12}$ alkyl group.

In one embodiment, $R^5$, $R^6$ and $R^7$ are independently selected from H or a $CH_3$ group and $R^8$ is H or a $C_1$-$C_4$ alkyl group. In still another embodiment, $R^5$, $R^6$ and $R^7$ are each a $CH_3$ group and $R^8$ is H, a methyl group, an ethyl group, a propyl group or an isopropyl group.

Examples of such compounds having formula (VIII), include, but are not limited to, 2,6-di-t-butyl-4-methyl phenol, 2,6-di-t-butyl-4-isopropyl phenol, 2,6-di-t-butyl-4-ethyl phenol, 2,4-dimethyl-6-octyl phenol, 2,6-di-t-butyl-4-n-butyl phenol and 2,4-dimethyl-6-t-butyl phenol.

In yet another embodiment, the treating agent is a mixture of at least one of a non-cyclic amide substituted with an isocyanate reactive group, a guanidine substituted with an isocyanate reactive group, a polyether amine adducted with a urea compound or guanidine compound described above with a sterically hindered phenol described above.

In some embodiments, the catalyst mixture of the amine catalyst and the treating agent is solid. Therefore a solvent may also be added when forming the catalyst mixture. The solvent is not limited and may include water, high molecular weight polyols, butanediol, alcohols, such as lower carbon chain alcohols, for example, isopropyl alcohol, ethanol, n-propyl alcohol, n-butyl alcohol, sec-butyl alcohol, n-amyl alcohol, sec-amyl alcohol, n-hexyl alcohol, and sec-hexyl alcohol; lower carbon chain alcohols that have been alkoxylated with ethylene oxide (EO), propylene oxide (PO) or butylene oxide (BO), for example, n-butanol+1EO, n-butanol+2EO, n-butanol+3EO, n-hexanol+6EO, 2-ethylhexanol+2EO and iso-butanol+3EO, alcohol ethers, polyalkylene alcohol ethers, such as ethylene glycol monobutyl ether, polyalkylene glycols, such as ethylene glycol and propylene glycol, poly(oxyalkylene) glycols, such as diethylene glycol, poly(oxyalkylene) glycol ethers, or any mixtures thereof. In one embodiment, the amount of solvent added may be an amount necessary to give a solids weight ratio of about 5-95% by weight. In another embodiment, the amount of solvent added may be an amount to give a solids weight ratio of about 10-80% by weight.

In one embodiment, the amine catalyst is treated by mixing it with the treating agent and optional solvent to form a catalyst mixture and then subjecting the catalyst mixture to conditions such that the level of aldehyde impurities in the amine catalyst is reduced.

According to one embodiment, such conditions include maintaining the catalyst mixture at approximately room temperature for a few hours to a few days. In one particular embodiment, the catalyst mixture is maintained at room temperature for at least about 3 hours. In another particular embodiment, the catalyst mixture is maintained at room temperature for at least about 6 hours. In still another embodiment, such conditions include maintaining the catalyst mixture at room temperature for at least about 12 hours, while in another embodiment such conditions include maintaining the catalyst mixture at room temperature for at least about 24 hours.

In other embodiments, a temperature higher than room temperature may be used to accelerate the removal of aldehydes from the catalyst mixture. Any temperature up to a temperature at which the amine catalyst degrades may be used. In one embodiment, the catalyst mixture is maintained at a temperature between about 25°-200° C.: for at least about 3 hours, in another embodiment for at least about 6 hours, in still another embodiment for at least about 12 hours, and yet in still another embodiment for at least 24 hours. In another embodiment, the catalyst mixture is maintained at a temperature between about 60°-150° C.: for at least about 3 hours, in another embodiment for at least about 6 hours, in still another embodiment for at least about 12 hours, and yet in still another embodiment for at least about 24 hours. In still another embodiment, the catalyst mixture is maintained at a temperature between about 80°-120° C.: for at least about 3 hours, in another embodiment for at least about 6 hours, in still another embodiment for at least about 12 hours, and yet in still another embodiment for at least about 24 hours.

In other embodiments, the catalyst mixture may be maintained at room temperature or a higher temperature such as described above and at atmospheric pressure or at a pressure up to about 3 atmosphere: for at least about 3 hours, in another embodiment for at least about 6 hours, in still another embodiment for at least about 12 hours, and yet in still another embodiment for at least about 24 hours.

In some embodiments, it's generally sufficient to treat the amine catalyst with about 0.005%-15% by weight treating agent based on the total weight of the catalyst mixture. In another embodiment, the amine catalyst may be treated with about 0.01%-10% by weight treating agent based on the total weight of catalyst mixture. In yet another embodiment, the amine catalyst may be treated with about 0.5%-5% by weight treating agent based on the total weight of catalyst mixture. In still another embodiment, the amine catalyst may be treated with up to about 10% by weight treating agent, while in other embodiments it may be treated up to about 7.5% by weight treating agent, each of which are based on the total weight of the catalyst mixture. In a further embodiment, the amine catalyst may be treated with at least about 0.05% by weight treating agent, in other embodiments it may be treated with at least about 1% by weight treating agent, each of which are based on the total weight of the catalyst mixture.

In still another embodiment, a formulation containing the amine catalyst together with other components useful in a polyurethane material formation reaction, for example, a polyol, a polyisocyanate, a surfactant, a blowing agent and/or other additives such as a cell stabilizer, crosslinking agent, chain extender, pigment, filler, flame retardant, mold release agent, plasticizers; acid scavenger; water scavenger; cell regulator; dye; UV stabilizer; fungistatic or bacteriostatic substance and transition metal catalyst may be treated with the treating agent and subjected to the conditions similar to those described above such that the level of aldehyde impurities in the formulation are reduced. Thus, in one embodiment, the amine catalyst and other components useful in a polyurethane formation reaction are mixed with the treating agent to form a formulation and then stored at room temperature or at a higher temperature of up to about 120° C.: for at least about 3 hours, in another embodiment for at least about 6 hours, in still another embodiment for at least about 12 hours, and yet still another embodiment for at least about 24 hours.

Once the level of aldehyde impurities in the catalyst mixture or formulation described above has been reduced, the catalyst mixture or formulation may be used to make a polyurethane material that exhibits reduced aldehyde emissions compared to a polyurethane material that has been made from a catalyst mixture or formulation that has not been treated in accordance with this disclosure. The catalyst mixture or formulation can be used to make polyurethane materials in the same manner as untreated materials.

These methods are well known to those skilled in the art and can be found in, for example, U.S. Pat. Nos. 5,420,170, 5,648,447, 6,107,359, 6,552,100, 6,737,471 and 6,790,872, the contents of which are hereby incorporated by reference. Various types of polyurethane materials can be made such as rigid foams, flexible foams, semi-flexible foams, microcellular elastomers, backings for textiles, spray elastomers, cast elastomers, polyurethane-isocyanurate foams, reaction injection molded polymers, structural reaction injection molded polymers and the like.

According to one embodiment, particular foam applications include foams for cushioning applications such as bedding and seating and foams for automotive interiors such as flexible and semi-flexible foams for automotive seating, in headrests, in dashboards and instrument panels, in armrests or in headliners.

In one particular embodiment, a polyurethane foam may be prepared by bringing together at least one polyol and at least one polyisocyanate in the presence of the catalyst mixture to form a reaction mixture and subjecting the reaction mixture to conditions sufficient to cause the polyol to react with the polyisocyanate. The polyol, polyisocyanate and catalyst mixture may be heated prior to mixing them to form the reaction mixture. In other embodiments, the polyol, polyisocyanate and catalyst mixture are mixed at ambient temperature (for e.g. from about 15°-40° C.). Heat may be applied to the reaction mixture, but in most embodiments, this is not necessary. The polyurethane foam may be made in a free rise (slabstock) process in which the foam is free to rise under minimal or no vertical constraints. Alternatively, molded foam may be made by introducing the reaction mixture in a closed mold and allowing it to foam within the mold. The particular polyol and polyisocyanate are selected with the desired characteristics of the resulting foam. Other components useful in making polyurethanes, such as those described above, may also be included to produce a particular type of foam.

According to one embodiment, the polyurethane material may be produced from the reaction of an A-side reactant with a B-side reactant. The A-side reactant may comprise a polyisocyanate while the B-side reactant may comprise a polyol and the catalyst mixture according to the present disclosure. In some embodiments, the A-side and/or B-side may also contain optional other components such as those described above.

The polyisocyanates suitable for use include unmodified polyisocyanates, modified polyisocyanates and isocyanate prepolymers. Such polyisocyanates include those represented by the formula Q(NCO)p where p is a number from 2-5, preferably 2-3 and Q is an aliphatic hydrocarbon group containing 2-18 carbon atoms, a cycloaliphatic hydrocarbon group containing 5-10 carbon atoms, an araliphatic hydrocarbon group containing 8-13 carbon atoms, or an aromatic hydrocarbon group containing 6-15 carbon atoms.

Examples of suitable polyisocyanates include, but are not limited to, ethylene diisocyanate; 1,4-tetramethylene diisocyanate; 1,6-hexamethylene diisocyanate; 1,12-dodecane diisocyanate; cyclobutane-1,3-diisocyanate; cyclohexane-1, 3- and -1,4-diisocyanate, and mixtures of these isomers; isophorone diisocyanate; 2,4- and 2,6-hexahydrotoluene diisocyanate and mixtures of these isomers; dicyclohexylmethane-4,4'-diisocyanate (hydrogenated MDI, or HMDI); 1,3- and 1,4-phenylene diisocyanate; 2,4- and 2,6-toluene diisocyanate and mixtures of these isomers (TDI); diphenylmethane-2,4'- and/or -4,4'-diisocyanate (MDI); naphthylene-1,5-diisocyanate; triphenylmethane-4,4',4"-triisocyanate; polyphenyl-polymethylene-polyisocyanates of the type which may be obtained by condensing aniline with formaldehyde, followed by phosgenation (crude MDI); norbornane diisocyanates; m- and p-isocyanatophenyl sulfonylisocyanates; perchlorinated aryl polyisocyanates; modified polyisocyanates containing carbodiimide groups, urethane groups, allophnate groups, isocyanurate groups, urea groups, or biruret groups; polyisocyanates obtained by telomerization reactions; polyisocyanates containing ester groups; and polyisocyanates containing polymeric fatty acid groups. Those skilled in the art will recognize that it is also possible to use mixtures of the polyisocyanates described above.

Isocyanate-terminated prepolymers may also be employed in the preparation of the polyurethane materials. Isocyanate prepolymers may be prepared by reacting an excess of polyisocyanate or mixture thereof with a minor amount of an active-hydrogen containing compound as determined by the well-known Zerewitinoff test as described by Kohler in "Journal of the American Chemical Society," 49, 3181 (1927).

The polyol may be a petroleum-derived polyol, a natural oil polyol or a polyol obtained from renewable natural resources such as vegetable oil.

Petroleum-derived polyols useful in producing a polyurethane material according to the present disclosure include polyether polyol, polymer polyols, and polyester polyols having 2 or more reactive hydroxyl groups. Polyether polyols include, for example, polyhydric alcohols such as glycol, glycerin, pentaerythritol, and sucrose; aliphatic amine compounds such as ammonia, and ethyleneamine; aromatic amine compounds such as toluene diamine, and diphenylmethane-4,4'-diamine; and/or a polyether polyol obtained by adding ethylene oxide or propylene oxide to a mixture of above-mentioned compounds. A polymer polyol is exemplified by a reaction product of a polyether polyol with ethylenic unsaturated monomer, such as butadiene, acrylonitrile, and styrene, the reaction being conducted in the presence of a radical polymerization catalyst. Polyester polyols include those which are produced from a dibasic acid and a polyhydric alcohol such as, for example, polyethyleneadipate and polyethyleneterephthalates which may include those products reclaimed from waste materials.

Polyols from inexpensive and renewable resources may also be used and are highly desirable since they minimize the depletion of fossil fuel and other non-sustainable resources. Natural oils consist of triglycerides of saturated and unsaturated fatty acids. One natural oil polyol is castor oil, a natural triglyceride of ricinoleic acid. Other natural oils need to be chemically modified to introduce sufficient hydroxyl content to make them useful in the production of polyurethane materials. There are two chemically reactive sites that can be considered when attempting to modify natural oil into a useful polyol: 1) the unsaturated sites (double bonds); and 2) the ester functionality. Unsaturated sites present in natural oil can be hydroxylated via epoxidation, followed by ring opening or hydroformilation, followed by hydrogenation. Alternatively, trans-esterification can also be utilized to introduce OH groups in natural oil. The chemical process for the preparation of natural polyols using an epoxidation route involves a reaction mixture that requires epoxidized natural oil, a ring opening acid catalyst and a ring opener. Epoxidized natural oils include epoxidized plant-based oils (epoxidized vegetable oils) and epoxidized animal fats. The epoxidized natural oils may be fully or partially epoxidized and these oils include soybean oil, corn oil, sunflower oil, olive oil, canola oil, sesame oil, palm oil, rapeseed oil, tung oil, cotton seed oil, safflower oil, peanut oil, linseed oil and combinations thereof. Animal fats include fish, tallow and lard. These natural oils are triglycerides of fatty acids which may be saturated or unsaturated with various chain lengths from $C_{12}$ to $C_{24}$. These acids can be: 1) saturated: lauric, myristic, palmitic, steric, arachidic and lignoceric; 2) mono-unsaturated: palmitoleic, oleic, 3) poly-unsaturated: linoleic, linolenic, arachidonic. Partially or fully epoxidized natural oil may be prepared when reacting peroxyacid under suitable reaction conditions. Examples of peroxyacids utilized in the epoxidation of oils have been described in WO 2006/116456 A1; hereby incorporated by reference. Ring opening of the epoxidized oils with alcohols, water and other compounds having one or multiple nucleophilic groups can be used. Depending on the reaction conditions, oligomerization of the epoxidized oil can also occur. Ring opening yields a natural oil polyol that can then be used in the manufacture of polyurethane materials. In the hydroformilation/hydrogenation process, the oil is hydroformylated in a reactor filled with a hydrogen/carbon monoxide mixture in the presence of a suitable catalyst (typically cobalt or rhodium) to form an aldehyde which is hydrogenated in the presence of cobalt or nickel catalyst to form a polyol. Alternatively, polyol from natural oil can be produced by trans-esterification with a suitable poly-hydroxyl containing substance using an alkali metal or alkali earth metal base or salt as a trans-esterification catalyst. Any natural oil or alternatively any partially hydrogenated oil can be used in the transesterification process. Examples of oils include, but are not limited to, soybean, corn, cottonseed, peanut, castor, sunflower, canola, rapeseed, safflower, fish, seal, palm, tung, olive oil or any blend thereof. Any multifunctional hydroxyl compound can also be used such as lactose, maltose, raffinose, sucrose, sorbitol, xylitol, erythritol, mannitol, or any combination.

In one particular embodiment, in addition to the polyol component and catalyst mixture, the B-side reactant optionally comprises one or more additives including, but not limited to: blowing agents; crosslinking agents, flame retardants; plasticizers; internal mold release agents; surfactants; acid scavengers; water scavengers; cell regulators; pigments; dyes; UV stabilizers; fungistatic or bacteriostatic substances; fillers and mixtures thereof.

Examples of blowing agents include, but are not limited to, water, liquid carbon dioxide, a hydrofluorocarbon, methyl isobutyl ketone, a low-boiling hydrocarbon such as pentane or cyclopentane, methylene chloride, a carbonate of an amine, or mixtures thereof.

Examples of crosslinking agents include, but are not limited to, ethylene glycol, diethylene glycol, triethylene glycol, propylene glycol, 1,3-propanediol, 1,4-butandiol, 1,6-hexanediol, glycerol, and trimethylolpropane.

Examples of flame retardants (which, as the term is used herein, also include smoke suppressants and other known combustion modifiers), include phosphonates, phosphites, and phosphates (such as dimethyl methylphosphonate, ammonium polyphosphate, and various cyclic phosphate and phosphonate esters known in the art); halogen-containing compounds known in the art (such as brominated diphenyl ether and other brominated aromatic compounds); melamine; antimony oxides (such as antimony pentoxide and antimony trioxide); zinc compounds (such as various known zinc borates); aluminum compounds (such as alumina trihydrate); and magnesium compounds (such as magnesium hydroxide).

Internal mold release agents are compounds that may be added to assist in the removal of the polyurethane material from a mold. Suitable internal mold release agents include those based at least in part on fatty acid esters, metal and/or amine salts of carboxylic acids, amido carboxylic acids, phosphorus-containing acids, boron-containing acids, amidines, and neutralized esters prepared from certain amine-started tetrahydroxy compounds as described in U.S. Pat. No. 5,208,268. Also suitable are water based and solvent based mold release agents, such as those containing naphthalene and paraffin wax.

Surfactants (or surface-active agents) include emulsifiers and foam stabilizers, such as silicone surfactants known in the art, for example, polysiloxanes, as well as various amine salts of fatty acids, such as diethylamine oleate or diethanolamine stearate, as well as sodium salts of ricinoleic acids.

Acid scavengers are compounds that may be added to control the acidity and water concentration. Preferred acid scavengers include various orthoesters, such as trimethyl orthoformate, carbodiimides, such as 2,2',6,6'-tetraisopropyldiphenylcarbodiimide, and epoxides, such as 3,4-epoxycyclohexylmethyl 3,4-epoxy-cyclohexylcarboxylate.

Water scavengers (or moisture scavengers) are compounds that may be added to maintain a low water content in the compositions of the present invention. Suitable water scavengers include alkali aluminosilicates.

Fillers and/or reinforcing substances, include barium sulfate, calcium carbonate, calcium silicate, aluminum hydroxide, titanium dioxide, clays, fly ash, kieselguhr, mica, glass fibers, liquid crystal fibers, glass flakes, glass balls, hollow microspheres made of glass, alumina, silicas, etc., aramide fibers, and carbon fibers.

According to one embodiment, the polyurethane material may be prepared in a one-step process in which an A-side reactant is combined with a B-side reactant. The A-side may include the polyisocyanate or mixture of polyisocyanates. Different polyisocyanates may be selected to create different properties in the final product. The B-side may be a solution including at least one polyol and the catalyst mixture of the present disclosure and optionally additives.

The polyurethane materials produced having reduced aldehyde emissions may be used in a variety of applications, such as, a precoat; a backing material for carpet; building composites; insulation; spray foam insulation; applications requiring use of impingement mix spray guns; urethane/urea hybrid elastomers; vehicle interior and exterior parts such as bed liners, dashboards, door panels, and steering wheels; flexible foams (such as furniture foams and vehicle component foams); integral skin foams; rigid spray foams; rigid pour-in-place foams; coatings; adhesives; sealants; filament winding; and other polyurethane composite, foams, elastomers, resins, and reaction injection molding (RIM) applications.

In another embodiment, there is provided a packaged product comprising: a) a container having at least an outlet; and b) the catalyst mixture of the present disclosure within the container.

According to one embodiment, the packaged product of the present disclosure comprises a container having a closure means, such as a lid, cover, cap, or plug to seal the container. In another embodiment, the sealed container also has a nozzle or pour spout. The sealed container may have the shape of a cylinder, oval, round, rectangle, canister, tub, square or jug and contains the catalyst mixture. In some embodiments, the sealed container is padded with an inert gas, such as nitrogen.

The container may be made from any material, such as steel, glass, aluminium, cardboard, tin-plate, plastics including HDPE, PP, PVC, PET, OPP, PE or polyamide and including mixtures, laminates or other combinations of these. The catalyst mixture is dispensed from the container through the outlet. In one embodiment, the catalyst mixture is dispensed from a nozzle when the nozzle is activated. In another embodiment, the catalyst is mixture is dispensed via a pour spout.

As described below, aldehydes, such as formaldehyde, can be reduced in the amine catalyst with no processing requirements other than mixing the amine catalyst with the treating agent and subjecting the mixture to normal storage conditions or elevated temperatures for a minimal amount of time.

EXAMPLES

Example 1a. Treating Agent 2847 grams of JEFFAMINE® D-400 polyether amine and 893 grams of urea were charged to a 5 liter flask equipped with a heating mantle, stirrer, temperature controller, nitrogen sparge tube, condenser and phosphoric acid ammonia trap. The material was heated to 124° C. Ammonia evolved in large amounts into the trap. The material was continually heated for 4.5 hours, with a slow raising of the temperature to 150° C. until the evolution of ammonia ceased. The material was analyzed by NMR and found to contain both primary amine and urea end groups with a trace of urea still present.

Example 1b. Treating Agent 500 grams of JEFFAMINE® D-2000 polyether amine was reacted with 326.3 grams of urea in the apparatus used in Example 1a. The temperature was slowly raised to 135° C. over eleven hours. The material obtained was a thick clear liquid that was pourable at 80° C. After analysis by NMR, it was found to contain both primary amine and urea end groups.

Example 1c. Treating Agent 6123 grams of monoethanol amine was reacted with 591 grams of urea in the apparatus described in Example 1a. The material was heated slowly to 80° C. with the temperature being increased over a 6 hour period to 112° C. to control the evolution of ammonia. The material was a waxy solid and analyzed by NMR and found to be ethanolurea.

Example 2. Control

N,N,N'-trimethyl-N'-hydroxyethylbisaminoethylether (JEFFCAT® ZF-10 amine catalyst) was analyzed and found to have a PtCo color of 131.6 and a formaldehyde content of 89.3 ppm. The amine catalyst was then placed in a one liter flask equipped with a nitrogen sparge tube, mixer, temperature controller, K head and condenser and distilled under vacuum. After analysis, the amine catalyst was found to have a PtCo color of 16.6 and a formaldehyde content of 96.1 ppm.

The formaldehyde measurements in this Example, as well as the other Examples, can be performed using known standard analytical tests, such as by trapping the formaldehyde on a media treated with dinitrophenyl hydrazine, desorbing with solvent, and measuring by liquid chromatography.

Example 3. Control 1000 grams of JEFFCAT® ZF-10 amine catalyst was placed in the same distillation apparatus used in Example 2. 400 grams of deionized water was then added to the flask and the mixture was distilled. After analysis, the amine catalyst was found to have a PtCo color of 18.4 and a formaldehyde content of 62.8 ppm.

Example 4. Amine Catalyst+Treating Agent 1000 grams of JEFFCAT® ZF-10 amine catalyst was added to the distillation apparatus used in Example 2 along with 400 grams of deionized water. 5 grams of 2,6-di-t-butyl-4-isopropyl phenol was then added and the mixture was distilled. After analysis, the amine catalyst was found to have a PtCo color of 31.6 and a formaldehyde content of 31.7 ppm.

Example 5. Amine Catalyst+Treating Agents 1000 grams of JEFFCAT® ZF-10 amine catalyst was added to the distillation apparatus used in Example 2 along with 400 grams of deionized water. 5 grams of 2,6-di-t-butyl-4-isopropyl phenol and 20 grams of a 50% w/w aqueous solution of ethanol urea from Example 1c were added and the mixture was distilled. After analysis, the amine catalyst was found to have a PtCo color of 19.2 and a formaldehyde content of 27.2 ppm.

The amine catalyst was then further treated with an additional 5 grams of 2,6-di-t-butyl-4-isopropyl phenol and 10 grams of a 50% aqueous ethanolurea from Example 1c and the mixture held at 100° C. for 24 hours. The amine catalyst was then analyzed and found to have a formaldehyde content of 23.7 ppm.

Example 6. Amine Catalyst+Treating Agent 1000 grams of JEFFCAT® ZF-10 amine catalyst was added to the distillation apparatus used in Example 2 along with 400 grams of deionized water. 20 grams of the treating agent prepared in Example 1a were added and the mixture was held at 100° C. for 24 hours. The amine catalyst was analyzed and found to have a formaldehyde content of 23.7 ppm.

Example 7. Low Density Foam

A low density wall spray foam was prepared by mixing 48.7 parts by weight of a A-side resin comprising Rubinate® M isocyanate with 51.3 parts by weight of an B-side formulation containing the following components:

| B-Side | Control pbw | i pbw |
| --- | --- | --- |
| JEFFOL ® SD-441* | 12.3 | 12.3 |
| JEFFOL ® G31-35* | 15.2 | 15.2 |
| Water | 22.0 | 22.0 |
| Fire Retardant Blend* | 25.0 | 25.0 |
| Silstab ® 2760 | 1.0 | 1.0 |
| Surfonic ® N-95* | 15.0 | 13.0 |
| JEFFCAT ® ZR-50* | 0.5 | 0.5 |
| JEFFCAT ® Z-110* | 4.0 | 4.0 |
| JEFFCAT ® S-127* | 5.0 | 5.0 |
| Treating Agent 1a | | 2.0 |
| Cream time, sec | 5 | 4.0 |
| Top of cup time, sec | 6.3 | 5.5 |
| Tack free time, sec | 9.9 | 9.3 |
| Rise time, sec | 10.3 | 10.7 |

*JEFFOL ® SD-441 is a sucrose polyol available from Huntsman International LLC
JEFFOL ® G31-35 is a glycerol initiated EO capped triol available from Huntsman International LLC
Fire Retardant Blend is a mixture of brominated and chlorinated phosphate ester
Silstab ® 2760 is a silicone surfactant available from Siltech Corp.
Surfonic ® N-95 is an ethoxylated nonyl phenol emulsifier available from Huntsman International LLC
JEFFCAT ® ZR-50, JEFFCAT ® Z-110 and JEFFCAT ® S-127 are tertiary amine catalysts available from Huntsman International LLC Good quality foam, with no detectable odor, was produced having a nominal density of 0.5 psf for formulations containing no treated catalyst and those containing a treated catalyst. Thus, use of the treated catalyst during the production of foam does not adversely affect foam quality.

Consideration must be given to the fact that although this disclosure has been described and disclosed in relation to certain preferred embodiments, obvious equivalent modifications and alterations thereof will become apparent to one of ordinary skill in this art upon reading and understanding this specification and the claims appended hereto. The present disclosure includes the subject matter defined by any combination of any one of the various claims appended hereto with any one or more of the remaining claims, including the incorporation of the features and/or limitations of any dependent claim, singly or in combination with features and/or limitations of any one or more of the other dependent claims, with features and/or limitations of any one or more of the independent claims, with the remaining dependent claims in their original text being read and applied to any independent claim so modified. This also includes combination of the features and/or limitations of one or more of the independent claims with the features and/or limitations of another independent claim to arrive at a modified independent claim, with the remaining dependent claims in their original text being read and applied to any independent claim so modified. Accordingly, the presently disclosed invention is intended to cover all such modifications and alterations, and is limited only by the scope of the claims which follow, in view of the foregoing and other contents of this specification.

What is claimed is:

1. A method for reducing the aldehyde content in an amine catalyst comprising (i) mixing an amine catalyst containing one or more aldehyde impurities and a treating agent selected from a polyether amine adducted with a urea compound or a guanidine compound to form a catalyst mixture and (ii) subjecting the catalyst mixture to conditions such that the level of aldehyde impurities in the catalyst mixture are reduced, wherein the polyether amine adducted with a urea compound or a guanidine compound is represented by the general formula (III):

$$R^4\text{—NH-A-NH}_2 \quad (III)$$

where $R^4$ is a linear or branched alkoxylated polyether polyamine, and
A is C=O or C=NH.

2. The method of claim 1 wherein the conditions include maintaining the catalyst mixture at approximately room temperature for at least about 3 hours.

3. The method of claim 1 wherein $R^4$ is an alkoxylated polyether polyamine represented by the general formula (IV):

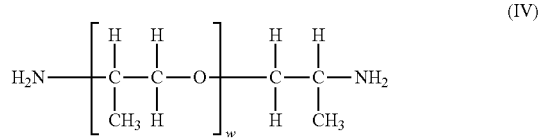

where w is an integer ranging from about 1.5 to about 150.

4. The method of claim 1 wherein the treating agent further comprises a free radical scavenger comprising a sterically hindered phenol having the formula (VIII):

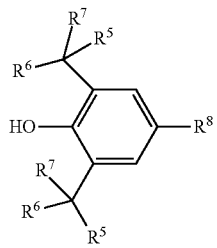

where $R^5$, $R^6$ and $R^7$ are independently selected from H or a $C_1$-$C_{10}$ alkyl group and $R^8$ is H or a $C_1$-$C_{12}$ alkyl group.

5. The method of claim 4 wherein $R^5$, $R^6$ and $R^7$ are independently selected from H or a $CH_3$ group and $R^8$ is H or a $C_1$-$C_4$ alkyl group.

6. The method of claim 4 wherein $R^5$, $R^6$ and $R^7$ are each a $CH_3$ group and $R^8$ is H, a methyl group, an ethyl group, a propyl group or an isopropyl group.

7. A method, for reducing the aldehyde content in an amine catalyst comprising (i) mixing an amine catalyst containing one or more aldehyde impurities and a treating agent selected from a polyether amine adducted with a urea compound or a guanidine compound to form a catalyst mixture and (ii) subjecting the catalyst mixture to conditions such that the level of aldehyde impurities in the catalyst mixture are reduced, wherein the polyether amine adducted with a urea compound or a guanidine compound is represented by the general formula (III):

$$R^4\text{—NH-A-NH}_2 \quad (III)$$

where $R^4$ is a linear or branched alkoxylated polyether polyamine, and
A is C=O or C=NH and wherein the conditions include maintaining the catalyst mixture at a temperature of between about 60°–150° C. for at least about 3 hours.

* * * * *